United States Patent [19]

Hempel et al.

[11] Patent Number: 4,851,391

[45] Date of Patent: Jul. 25, 1989

[54] 5-ETHYL-2-DEOXYURIDINE AND UREA COMPOSITION FOR THE TREATMENT OF VIRAL DISEASES

[75] Inventors: Bernd Hempel; Ravindernath Kaul, both of Esslingen-Zell, Fed. Rep. of Germany

[73] Assignee: ROBUGEN GmbH Pharmazeutische Fabrik, Esslingen, Fed. Rep. of Germany

[21] Appl. No.: 161,037

[22] Filed: Feb. 26, 1988

[30] Foreign Application Priority Data

Feb. 27, 1987 [DE] Fed. Rep. of Germany ....... 3706421

[51] Int. Cl.$^4$ .................... A61K 31/70; A61K 31/00; A61K 7/40
[52] U.S. Cl. ..................................... 514/50; 514/588; 514/947
[58] Field of Search ........................ 514/50, 588, 947

[56] References Cited

U.S. PATENT DOCUMENTS

| | | | |
|---|---|---|---|
| 4,239,761 | 12/1980 | Rebling et al. | 514/256 |
| 4,309,989 | 1/1982 | Fahim | 514/494 |
| 4,424,232 | 1/1984 | Parkinson | 514/474 |
| 4,652,557 | 3/1987 | Sandborn | 514/164 |
| 4,708,965 | 11/1987 | Morgan | 514/563 |

OTHER PUBLICATIONS

Schinazi et al., Antimicrobial Agents and Chemotherapy 28, pp. 552–560, (1985).

*Primary Examiner*—Ronald W. Griffin
*Assistant Examiner*—Jenny Tou
*Attorney, Agent, or Firm*—Birch, Stewart, Kolasch & Birch

[57] ABSTRACT

Novel medicinal agent for the topical treatment of viral diseases, containing 5-ethyl-2'-deoxyuridine as the antivirally active compound and urea as the penetration-promoting compound, in an aqueous gel.

4 Claims, No Drawings

5-ETHYL-2-DEOXYURIDINE AND UREA COMPOSITION FOR THE TREATMENT OF VIRAL DISEASES

The present invention relates to a novel medicinal agent for the treatment of viral diseases in man and animals, especially diseases caused by herpes viruses (HSV).

In order to be able to effectively combat viral disease of the skin and mucous membrane, it is necessary for an antivirally active compound to reach the site of the herpes virus infection with maximum speed upon the first signs of such disease.

It is known that most of the antiherpes drugs show, in vitro, good antiviral activity, but fail in vivo or in clinical tests. The reason in most instances resides in that the active compounds do not reach the site of the disease and thus are not available, in a sufficiently high concentration for combating the viruses.

Locally applied antiherpes drugs must first pass through the skin barrier or mucosa barrier to get to the more deeply seated site of infection. Active agents having antiherpes activity in simple medicinal preparations for local application, such as, for example, creams, ointments or gelts, do not by themselves penetrate adequately and therefore show only low efficacy as compared with the in vitro test.

Thus, for example, the compound 5-ethyl-2'-deoxyuridine (EDU) proved to be satisfactorily effective in a cell culture against HSV Type 1 and Type 2. The compound has low toxicity and, after absorption, is quickly metabolized and excreted. However, problems were encountered in the topical treatment of herpes virus infections of the skin with 5-ethyl-2'-deoxyuridine (EDU). The efficacy was not as extensive as could be expected judging by the efficacy in the cell culture.

Therefore, attempts have been made to produce a more effective preparation by the addition of penetration-enhancing compounds.

Tests were made, for example, with dimethyl sulfoxide (DMSO) 100%, as well as azone 5% in water. Tests for efficacy in hairless mice cutaneously infected with HSV-1 and HSV-2 shows that 5% azone as well as DMSO had no effect on the effectiveness of EDU in this pharmacological model.

Therefore, it is an object of this invention to improve an antiviral medicinal agent containing 5-ethyl-2'-deoxyuridine as the antivirally active agent in such a way that it is usable for the topical treatment of viral diseases, wherein especially the bioavailability of the antivirally active agent is markedly improved. It has now been discovered surprisingly that an addition of 3-7% by weight, especially 5% by weight, of urea decisively increases the penetration of EDU into the skin. This could be demonstrated, for example, on a guinea pig skin test model with the aid of HPLC (high performance liquid chromatography). In these tests, a gel was utilized having varying contents of EDU and urea. Conventional gel-forming bases were used, such as, for example, polyacrylic acid, carboxymethylcellulose, etc., in water.

The test results confirm that EDU penetration is significantly increased in the presence of 3-7% by weight of urea, based on the total weight of the gel. Based on these test results, EDU is practically not at all metabolized in the skin. These results are supported by investigating the penetration into guinea pig skin with the aid of $C^{14}$-labeled EDU. Also for these tests, a gel was employed containing 1.2% by weight; 3% by weight; of 5% by weight of EDU and 3-7% by weight of urea. (The percentage data included in this application are based on the total weight of the pharmaceutical agent, e.g. the gel.)

It can be seen, surprisingly, from the test results that the skin penetration of EDU in all cases was markedly better in the presence of urea than without area, or than in the presence of other compounds assumed to promote penetration. It was likewise surprisingly that a gel containing 3% of EDU and 5% of urea was better than a gel with 1.2% EDU and 5% urea, or a gel containing 5% EDU and 5% urea. These results were supported by tests on hairless mice cutaneously infected with HSV-1. Here again, the gel preparations which proved to be most effective were those containing 1-5% by weight, especially 3% by weight EDU and 3-7% by weight, especially 5% urea.

The combination of a nucleoside-analogous antivirus drug (EDU) with urea as the penetration-enhancing compound in a gel is novel, and the good efficacy of the novel medicinal agent could not be foreseen. The advantages attained by the invention consist particularly in that optimum efficacy is achieved with a low dose of the active compound EDU of 1-5% by weight, especially 3% by weight. Thus, the diseased organism is not additionally burdened by foreign substances.

The aqueous gel combines good compatibility at a low EDU concentration with good penetration and maximizing efficacy.

Suitable gel-forming bases are conventional gel-forming compounds, such as polyacrylic acid, carboxymethylcellulose, hydroxyethylcellulose, methylcellulose, methylhydroxyethylcellulose or methylhydroxypropylcellulose in water.

The following examples are representative of the invention, but is in no way trying to be construed as limiting its scope.

Topical treatment of cutaneous HSV-1 infection in hairless mice

Hairless mice, 25-30 days old, having a body weight of 15-20 g were inoculated intracutaneously in the lumbosacral area with HSV-1 (KOS) at $10^{4.7}$ PFU/0.05 ml/mouse and were treated topically with the following compositions four times a day for five days, starting immediately after virus infection. The compositions used were as follows:

| EDU-Urea Gel (3%/5%): Formula of 100 g Gel: | |
|---|---|
| 5-Ethyl-2'-deoxyuridine | 3.0 g |
| Urea | 5.0 g |
| Benzalkonium chloride | 0.01 g |
| Sodium edetate | 0.1 g |
| Polyacrylic acid (Carbopol 940) | 0.5 g |
| Sodium hydroxide | 0.16 g |
| Water for injection | 93.03 g |

EDU-Gel (3%):
Same formula as indicated above for the EDU-Urea-Gel except urea was replaced by the same amount of water for injection.

Placebo:
Same formula as indicated above except 5-Ethyl-2'-deoxyuridine and urea were replaced by the same amounts of water for injection.

The effect of the aforementioned compositions on the development of herpetic skin lesions, paralysis of the hind legs and mortality of the mice was recorded. The results are summarized in the following table:

| Composition | | Number of mice without lesions (N: normal), with skin lesions (L), with skin lesions plus paralysis (P), or dead (D) on the following day after virus inoculation | | | | | | | | | | | | | | | | | | | | | Survival rate of the 20th day |
|---|---|---|---|---|---|---|---|---|---|---|---|---|---|---|---|---|---|---|---|---|---|---|---|
| | Day No.: | 0 | 1 | 2 | 3 | 4 | 5 | 6 | 7 | 8 | 9 | 10 | 11 | 12 | 13 | 14 | 15 | 16 | 17 | 18 | 19 | 20 | |
| EDU-UREA-gel 3%-5% | N | 5 | 5 | 5 | 5 | 4 | 3 | 3 | 2 | 1 | 1 | 1 | 1 | 1 | 1 | 1 | 1 | 1 | 1 | 1 | 1 | 1 | 2/5 |
| | L | — | — | — | — | 1 | 2 | 2 | 2 | 3 | 2 | 2 | 1 | 1 | 1 | 1 | 1 | 1 | 1 | 1 | 1 | 1 | |
| | P | — | — | — | — | — | — | — | 1 | 1 | 2 | 1 | — | — | — | — | — | — | — | — | — | — | |
| | D | — | — | — | — | — | — | — | — | — | 1 | 3 | 3 | 3 | 3 | 3 | 3 | 3 | 3 | 3 | 3 | 3 | |
| EDU-gel 3% | N | 5 | 5 | 5 | 5 | 4 | 3 | — | — | — | — | — | — | — | — | — | — | — | — | — | — | — | 1/5 |
| | L | — | — | — | — | 1 | 2 | 5 | 4 | 3 | 1 | 1 | 1 | 1 | 1 | 1 | 1 | 1 | 1 | 1 | 1 | 1 | |
| | P | — | — | — | — | — | — | — | 1 | 2 | 1 | 1 | — | — | — | — | — | — | — | — | — | — | |
| | D | — | — | — | — | — | — | — | — | — | 3 | 3 | 4 | 4 | 4 | 4 | 4 | 4 | 4 | 4 | 4 | 4 | |
| Placebo (no treatment) | N | 5 | 5 | 5 | 5 | 3 | — | — | — | — | — | — | — | — | — | — | — | — | — | — | — | — | 0/5 |
| | L | — | — | — | — | 2 | 3 | — | — | — | — | — | — | — | — | — | — | — | — | — | — | — | |
| | P | — | — | — | — | — | 1 | 4 | 3 | — | — | — | — | — | — | — | — | — | — | — | — | — | |
| | D | — | — | — | — | — | 1 | 1 | 2 | 5 | 5 | 5 | 5 | 5 | 5 | 5 | 5 | 5 | 5 | 5 | 5 | 5 | |

EXAMPLES (1)
100 g of gel contains:

| | |
|---|---|
| 5-Ethyl-2'-deoxyuridine | 3.0 g |
| Urea | 5.0 g |
| Benzalkonium chloride | 0.01 g |
| Sodium edetate | 0.1 g |
| Polyacrylic acid ("Carbopol" 940) | 0.5 g |
| Sodium hydroxide | 0.16 g |
| Water for injection | 93.03 g |

(2)
100 g of gel contains:

| | |
|---|---|
| 5-Ethyl-2'-deoxyuridine | 3 g |
| Urea | 5 g |
| Carboxymethylcellulose Sodium 600 | 5 g |
| Glycerol, 85% strength | 10 g |
| Sorbic acid | 0.1 g |
| Potassium sorbate | 0.1 g |
| Water | 76.8 g |

(3)
100 g of gel contains:

| | |
|---|---|
| 5-Ethyl-2'-deoxyuridine | 2 g |
| Urea | 6 g |
| Hydroxymethylcellulose 30,000 | 2.5 g |
| Glycerol, 85% strength | 10.0 g |
| Sorbic acid | 0.1 g |
| Potassium sorbate | 0.1 g |
| Water | 79.3 g |

(4)
100 g of gel contains:

| | |
|---|---|
| 5-Ethyl-2'-deoxyuridine | 5.0 g |
| Urea | 3.0 g |
| Hydroxypropylcellulose 30,000 | 2.5 g |
| Glycerol, 85% strength | 10.0 g |
| Sorbic acid | 0.1 g |
| Potassium sorbate | 0.1 g |
| Water | 79.3 g |

We claim:

1. A pharmaceutical composition for the topical treatment of viral diseases in man and animals, consisting of an antivirally effective amount of 5-ethyl-2'-deoxyuridine and a penetration-promoting amount of urea in a gel forming base.

2. The pharmaceutical composition according to claim 1 wherein said antiviral effective amount of 5-ethyl-2'-deoxyuridine comprises 1–5% by weight, and said penetration promoting amount of urea comprises 3–7% by weight, in an aqueous gel forming base.

3. A method of treating a viral disease in a mammal which comprises administering an antiviral effective amount of the composition according to claim 1.

4. The method according to claim 3 wherein said viral disease is caused by HSV-1.

* * * * *